United States Patent [19]

Nelson et al.

[11] Patent Number: 5,719,916
[45] Date of Patent: Feb. 17, 1998

[54] ANTHROPOMORPHIC MAMMOGRAPHY AND LUNG PHANTOMS

[76] Inventors: Robert S. Nelson, 2922 Upshur St., San Digeo, Calif. 92106; Reuven D. Zach, 1039 N. Harper Ave., #8, Los Angeles, Calif. 90046

[21] Appl. No.: 470,353

[22] Filed: Jun. 5, 1995

[51] Int. Cl.⁶ ................................... G01D 18/00
[52] U.S. Cl. ............................................ 378/207
[58] Field of Search .................... 434/267–272, 434/218; 378/18, 207; 250/252.1 R

[56] References Cited

U.S. PATENT DOCUMENTS

| | | | |
|---|---|---|---|
| 3,310,885 | 3/1967 | Alderson | 434/267 |
| 5,266,035 | 11/1993 | Olsen et al. | 434/272 |
| 5,273,435 | 12/1993 | Jacobson | 434/262 |

OTHER PUBLICATIONS

"Tissue substituted in experimental radiation physics", D.R. White; Medical Physics; Nov. 1978, pp. 467–479.
"Phantom for a Use in Lung Biopsy Training", Scott, Jr., Jul. 1992, pp. 286–287.
"The Phantom Patient for comprehensive basic training of radiologic technologists", Alderson Radiography Phantoms, 1979–1980, pp. 2–8.
"A Review of Mammography Test Objects for the Calibration of Resolution, Contrast, and Exposure," by Carolyn Kimme-Smith, Lawrence W. Bassett, and Richard H. Gold.

Primary Examiner—Don Wong
Attorney, Agent, or Firm—Lyon & Lyon LLP

[57] ABSTRACT

The present invention provides an apparatus and a method of use and construction of Anthropomorphic Mammography and Lung Phantoms. The phantoms resolve deficiencies that currently exist in the practice of mammography and lung x-ray imaging. The mammography phantom provides mammography practitioners a training tool in the practice of proper patient breast positioning and in optimal patient x-ray exposure. The mammography phantom can be used to generate x-ray images similar to mammography patient x-ray images. The mammography phantom simulates normal breast tissue and tissue irregularities and anomalies associated with various known breast pathologies such as microcalcifications, cysts, tumors, etc. The mammography phantom preferably comprises the shape of an upper torso of a woman including one or two breast simulators which can vary in size, density, compressibility, and stretchability. The mammography phantom is preferably constructed such that the breast simulators can be detached from the upper torso phantom (which can include articulating arms) and replaced, enabling the mounting of a variety of breast simulator types. The upper torso of the mammography phantom also provides a rib cage (with pectoralis major muscle) for the mounted breast simulators, providing an additional element of realistic patient simulation. The lung phantom is a lung simulator which can be used with presently available human upper torso phantoms having an empty cavity into which the lung phantom can be inserted. The lung phantom provides fine x-ray patterns and anomalies in simulation of actual lung x-ray images.

37 Claims, 5 Drawing Sheets

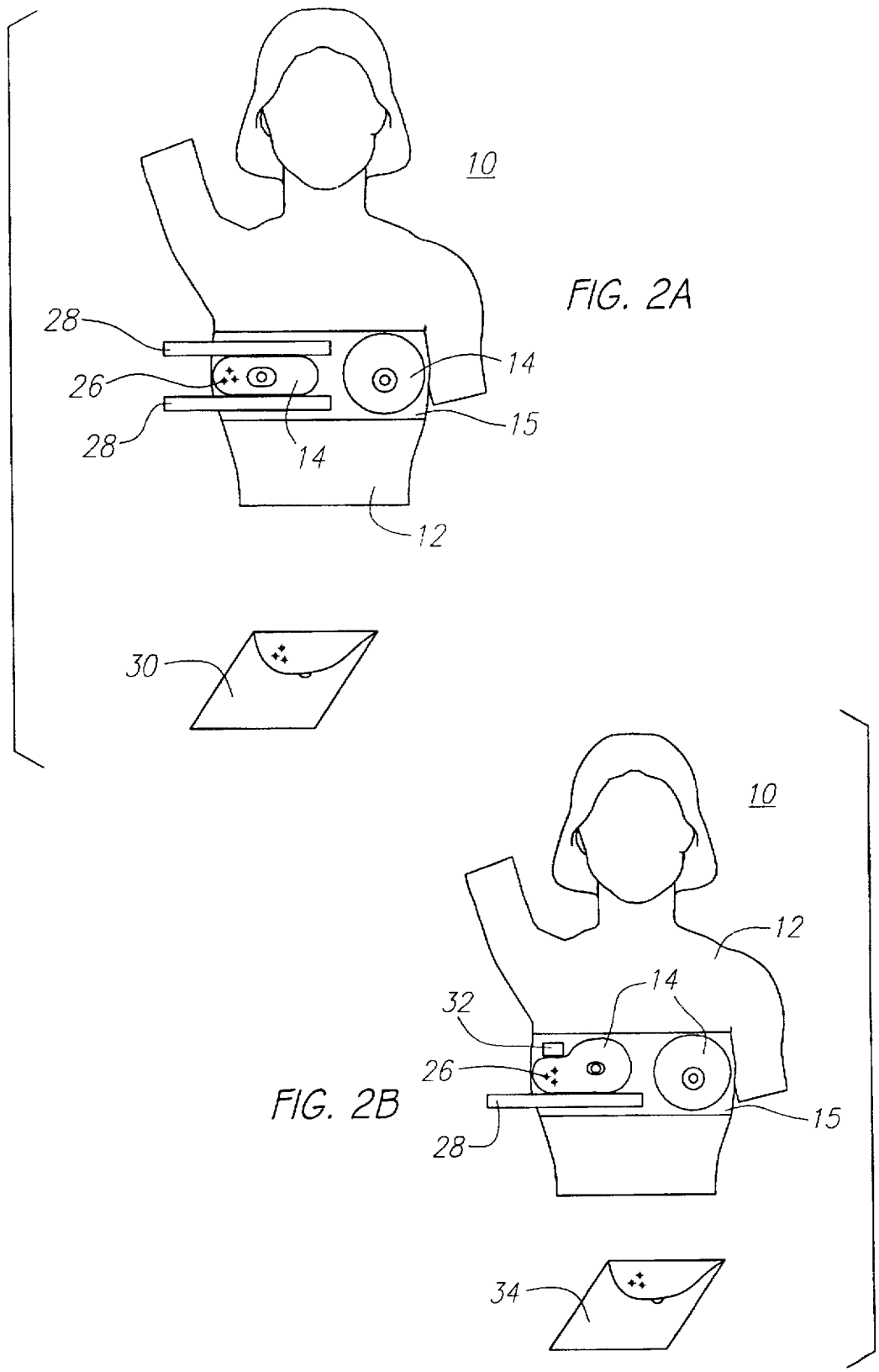

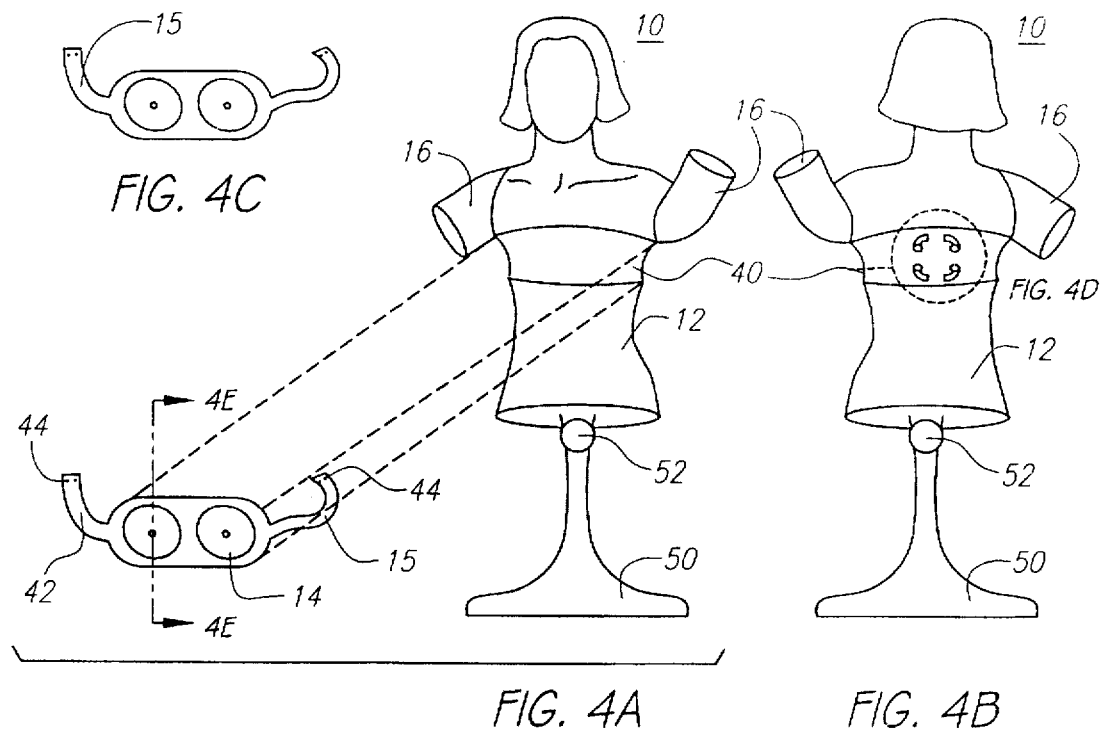
FIG. 4C
FIG. 4A
FIG. 4B
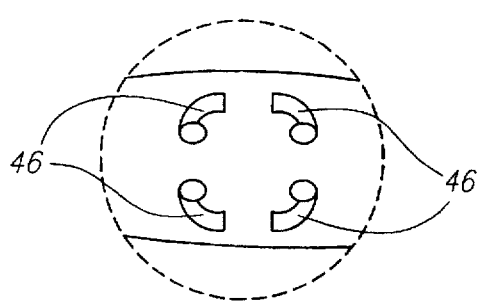
FIG. 4D
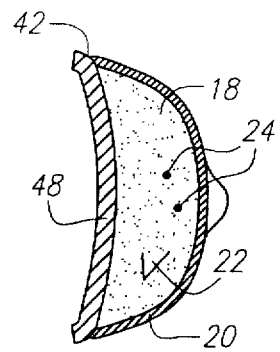
FIG. 4E
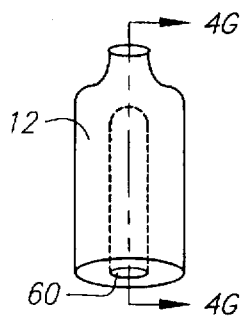
FIG. 4F
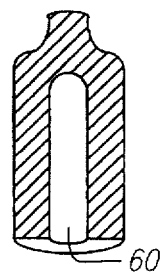
FIG. 4G
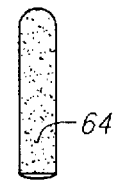
FIG. 4H

ANTHROPOMORPHIC MAMMOGRAPHY AND LUNG PHANTOMS

FIELD OF INVENTION

The present invention relates to phantoms, particularly anthropomorphic phantoms for training and calibration use in mammography applications and in lung x-ray applications.

BACKGROUND

Phantoms, in general, play a major role in radiology. Typically, phantoms are used to provide a tool for the assessment and verification of performance standards in daily clinical practice of radiology with respect to the quality of a radiological image and the quantity of an absorbed dose. This is true for general radiology practice, and more so for mammography and lung applications. The purpose of using phantoms in general radiology is to simulate a patient. However, those phantoms intended for general radiology uses are acutely deficient when directed for use in mammography and lung applications. Presently the only phantoms used with mammography are calibration or test phantoms. Phantoms which mimic lung organs within a human torso are not presently available. Not all aspects of mammography or lung x-ray applications are addressed by these phantoms.

While proper calibration of the equipment used in mammography is important (as it is in all x-ray applications), proper breast positioning and proper breast compression are very important as breasts are difficult objects to image and images of breasts are difficult to review. The importance of positioning and compression has been described by those in the industry as being "of paramount importance", "crucial", and "critical" to achieving a usable mammogram.

"Correct patient positioning is of paramount importance in mammography. The breast must be pulled away from the chest wall by the technologist, while compression, vigorous, and, it is hoped, painless, is applied . . . [I]f the technologist is not adept and aggressive in positioning the patient, the mammogram will be inadequate."
Kimme-Smith, et al., *Workbook for Quality Mammography* 2 (1986). "One-third of the facilities that seek ACR [American College of Radiology] approval do not initially pass muster; in some cases technologists were not adequately trained to position and compress the breast. These skills are crucial because proper compression provides clear, easy-to-interpret views of the breast using the smallest possible dose of radiation. In other centers it's the machines, not the people, that are problematic. Nearly one out of six facilities are initially rejected by the ACR because their equipment is not accurately calibrated."
Harvard Health Letter, Vol. 19 No. 9, July 1994, p. 3.

". . . Experienced radiologists concede that dense breasts are more difficult to image, but believe that good technique enhances mammography's ability to detect cancer in this tissue . . .

. . . 80% of women at age 30 have a dense pattern. The percentage drops to 70% by age 40 and 60% by age 60. By age 60, about half of all women have a fatty pattern and half a dense pattern . . .

The dense breast presents a special technical challenge to mammographers. Because it contains a lot of fibrous tissue, it has less inherent contrast than the fatty breast. Further, cancers often display similar x-ray attenuation to fibrous, glandular [dense] tissue, making them difficult to detect . . .

Successful imaging of the dense breast begins with taught compression . . . The denser the breast, the more critical adequate compression becomes. Compression helps prevent superimposition of tissue, decreases the amount of scattered radiation, and brings an abnormality closer to the image receptor. The result is a sharper image."
D'Agincourt, *Technique Is Everything When Breast Is Dense*, Diagnostic Imaging 57, 57–58 (September 1993).

Despite recognition of these requirements, phantoms which are currently available for use in mammography do not provide a realistic tool for radiologists to use to train in the proper positioning and/or compressing of breast tissue for mammography purposes.

In addition, the tools currently available for mammography are calibration tools which are designed and limited to the purpose of calibrating the mammography x-ray imaging chain. See, e.g., Kimme-Smith, et al., *A Review of Mammography Test Objects for the Calibration of Resolution, Contrast, and Exposure*, Medical Phys. 758–65 (September/ October 1989). Calibration phantoms which are currently available are typically merely blocks of plastic (e.g. acrylic) having tissue equivalent x-ray radiation absorption and/or scattering properties to which may be added grains (e.g. calcium and/or aluminum salts) of varying sizes, e.g., 0.2, 0.5, 0.7, and 1.0 mm. Such phantoms do not have the look or feel of human breasts and do not produce realistic images comparable to patient mammographic images. Therefore, such phantoms do not provide opportunities for developing or improving the positioning skills of mammography technologists, do not provide for developing or improving diagnostic skills of mammogram image interpreters, and do not provide a realistic tool for the calibration of diagnostic mammographic x-ray equipment.

In addition, as is mentioned above, there are no available anthropomorphic phantoms which mimic the x-ray radiographic imaging qualities of human lung tissue within a human torso. The closest phantoms are those which generally attempt to duplicate a human torso. Such phantoms may typically include model bone structures and an empty cavity in an attempt to simulate air-filled lungs. However, such empty-cavity phantoms do not furnish fine x-ray patterns as are generally produced in x-ray images of actual lung tissue and, therefore, do not provide for developing or improving diagnostic skills of lung x-ray interpreters.

SUMMARY OF THE INVENTION

The present invention comprises anthropomorphic phantoms for use in conjunction with mammography and lung x-ray applications. The anthropomorphic phantoms of the present invention address the above described problems and solve other limitations in the current state of the art of ancillary tools employed in mammography and lung x-ray applications. The present phantoms enhance training and practice of proper patient positioning and patient x-ray exposure. They also can be used to hone a radiologist's ability to detect irregularities in breast tissue and lung tissue. They further provide better phantoms for use in calibrating mammography and x-ray equipment. With the aid of the present phantoms reliability and sensitivity of breast and lung screening examinations may be improved.

The preferred embodiment of the anthropomorphic mammography phantom of the present invention has the shape of an upper torso of a woman including a phantom breast simulator preferably comprising a pair of simulated breasts (which can be substantially similar to or very different from each other) and which can be varied in size and stiffness (from small to large and from stiff to pendulous), density and firmness, compressibility and stretchiness. The phantom breast simulators are preferably made of materials which mimic the x-ray opacity and density of breast tissue or which have x-ray opacity similar to the x-ray opacity of tissue. Optionally, density variations representing tissue irregularities can be added to the breast simulators. Further, the mammography phantom may include a selective attachment mechanism enabling various breast simulators to be attached to and detached from the phantom.

The presently described preferred embodiment lung phantom includes a lung simulator plug which is preferably made of materials which mimic the x-ray opacity of lung tissue or which have x-ray opacity similar to the x-ray opacity of tissue. Optionally, density variations representing tissue irregularities may be added to the lung simulator plug. The lung simulator plug is preferably used in conjunction with an empty-cavity chest phantom described above and presently used in the art (i.e. by inserting a lung simulator plug into the empty lung cavity of such a phantom).

The anthropomorphic breast phantom of the present invention can be used to practice positioning and compression of breasts for mammography purposes, to produce mammographic images similar to mammography x-ray images of patients, and to calibrate equipment used in mammography. Therefore, with the aid of the present phantom, a technologist can practice realistic positioning and compression of a breast to produce the best mammographic images (as described above and in other references); radiologists can hone their diagnostic skills in reviewing and interpreting breast images; and mammography equipment can be calibrated.

The anthropomorphic lung phantom of the present invention can be used to produce chest x-ray images similar to chest x-ray images of patients. Therefore, with the aid of the present lung phantom, radiologists can hone their diagnostic skills in reviewing and interpreting lung x-ray images.

It is, therefore, a primary object of the present invention to provide an improved anthropomorphic phantom which substantially mimics the x-ray radiographic imaging properties of certain human organs.

It is an additional object of the present invention to provide an anthropomorphic phantom to use in mammography applications.

It is also an object of the present invention to provide an anthropomorphic lung phantom to use in lung x-ray applications.

It is a further object of the present invention to provide an anthropomorphic phantom which enhances training and practice of proper patient positioning.

It is another object of the present invention to provide an anthropomorphic phantom which enhances training and practice of proper patient x-ray exposure.

It is also an object of the present invention to provide an anthropomorphic mammography phantom which can be used to teach, test, and/or improve radiologists' ability to detect breast tissue irregularities.

It is still another object of the present invention to provide an anthropomorphic phantom which can be used to teach, test, and/or improve radiologists' ability to detect lung tissue irregularities.

It is yet a further object of the present invention to provide a phantom for use in calibrating x-ray equipment.

Other objects and features of the present invention will become apparent from consideration of the following description taken in conjunction with the accompanying drawings.

BRIEF DESCRIPTION OF THE DRAWINGS

FIG. 2A is a front view of a breast phantom showing a breast simulator subjected to standard mammography compression and an x-ray image which may result from the same and which shows unresolved overlap of tissue abnormalities in the breast simulator.

FIG. 2B is a front view of a breast phantom showing a breast simulator subjected to spot compression and an x-ray image which may result from the same and which shows resolved images of the tissue abnormalities in the breast simulator due to the compression.

FIG. 4A is a front perspective view of a breast phantom of the present invention.

FIG. 4B is a back perspective view of a breast phantom of the present invention.

FIG. 4C is a perspective view of a removable unit comprising two breast simulators of the present invention.

FIG. 4D is an enlarged view of the breast simulator unit attachment mechanism shown in FIG. 4B.

FIG. 4E is a cross-sectional view of a breast simulator taken along line 4E—4E in FIG. 4C.

FIG. 4F is a front perspective view of a typical currently available chest phantom showing the torso cavity of the same.

FIG. 4G is a cross-sectional view of the torso cavity of the chest phantom shown in FIG. 4F taken along line 4G—4G in FIG. 4F.

FIG. 4H is a perspective view of the lung simulator plug of the present invention.

DETAILED DESCRIPTION OF THE PREFERRED EMBODIMENT

Figure 1A:
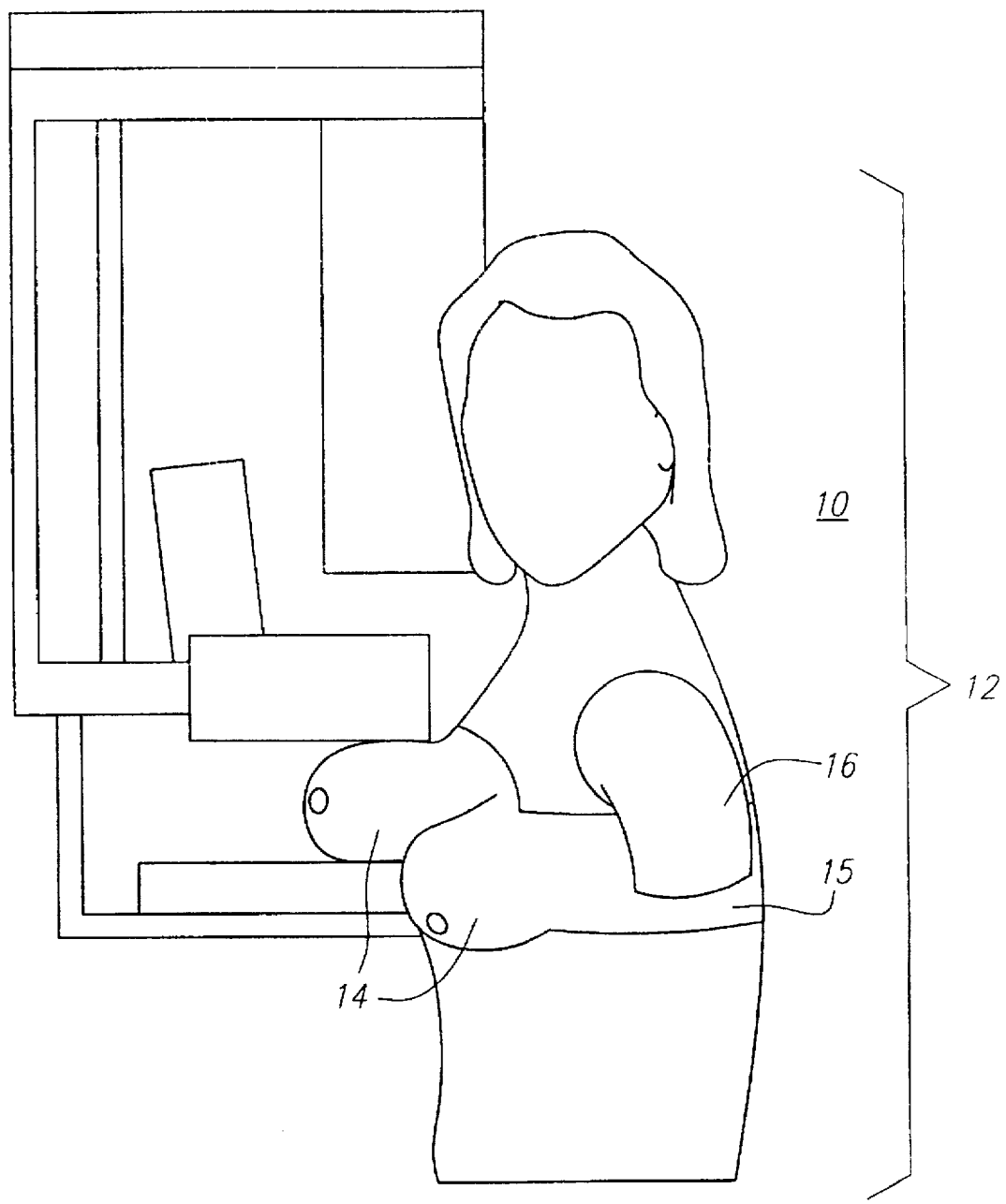
FIG. 1A is a perspective view of a preferred embodiment of the present mammography phantom with a detachable breast simulator positioned for x-ray examination.
Figure 1B:
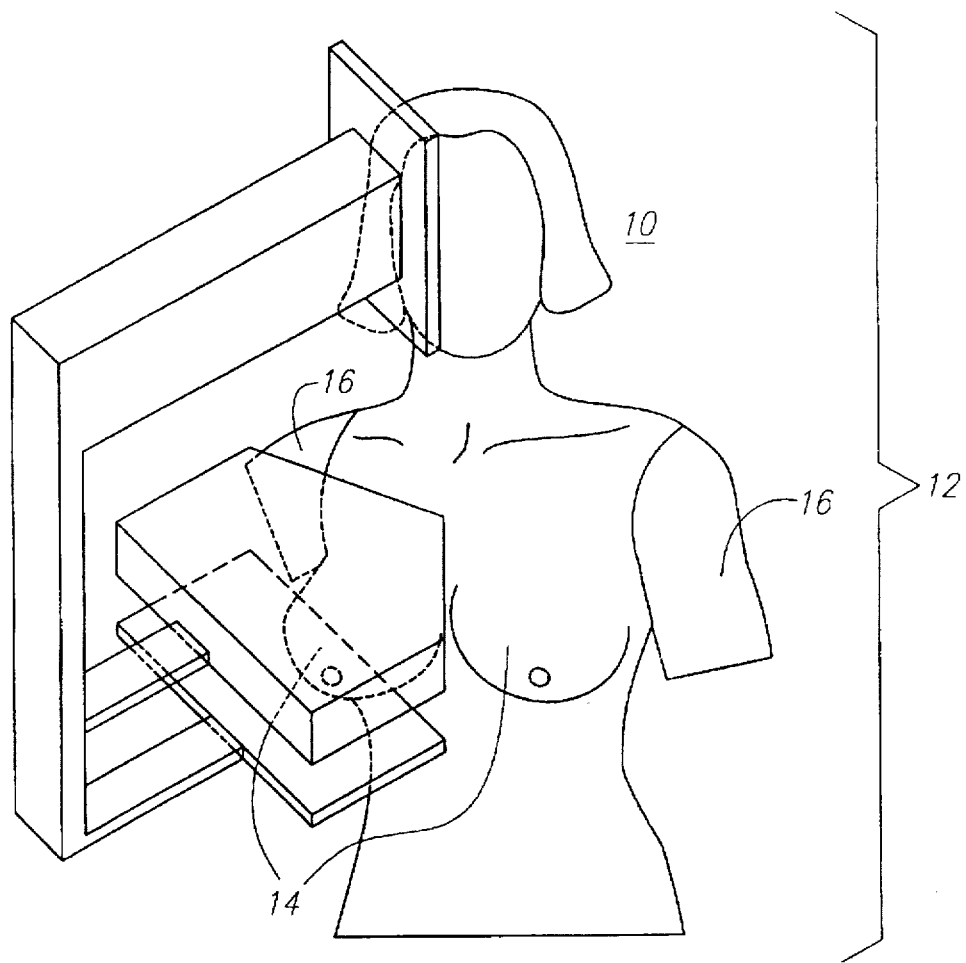
FIG. 1B is a perspective view of a second embodiment of the anthropomorphic mammography phantom of the present invention with a breast simulator positioned for x-ray examination.

Turning now to the drawings in detail, FIGS. 1A, 1B, and 4A show alternative embodiments of the anthropomorphic mammography phantom 10 of the present invention. As is shown in FIGS. 1A and 1B, the phantom 10 preferably substantially simulates a human female upper torso and more particularly, comprises an upper torso 12 which includes a pair of breast simulators 14 and which can include adjustable arms 16 (to help mimic patient movement of stretching chest and breast ligaments). The pair of breast simulators 14 preferably comprises a detachable unit 15 as is shown in FIGS. 1A, 4A, and 4C. Although the preferred embodiment includes a pair of breast simulators 14 a phantom can have one or more breast simulators.

Figure 1C:
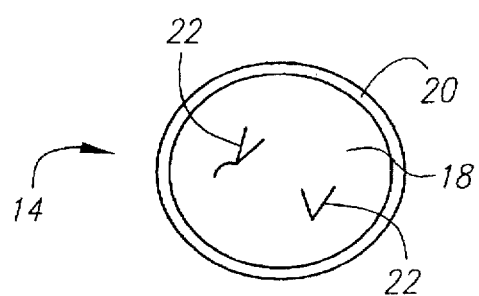
FIG. 1C is a cross-sectional view of a breast simulator of the present invention.

As is shown in FIGS. 1C and 4E, each breast simulator 14 comprises one or more suitable core materials 18 (such as plastic foam, sponge, foam, gel, etc.) encased by a textured skin-like cover 20 and preferably contains additional structures 22 embedded in or attached to the core materials 18. Each breast simulator 14, including core material 18 and skin-like cover 20, simulates mechanical and x-ray properties of a human breast, however, they need not be substantially identical to each other. Breast simulators 14 preferably comprise the following materials: The core material 18 is preferably a spongy malleable foam which has elastic properties causing it to (substantially) return to its original state after compression or manipulation ceases. A suitable material is polyurethane foam which is readily available. The skin-like cover 20 preferably comprises latex, which is readily available. The embedded structures 22 are preferably x-ray absorbent materials such as grains of metal salts (e.g. calcium or aluminum salt grains) or crushed egg shells which can be glued onto the foam or injected therein, such metal salts and egg shells are readily available. Additional embedded materials can include a metallic fine wool such as aluminum or steel or copper wool which can be layered between the foam interior 18 and latex exterior 20 or which can be integral to the foam interior 18. Further embedded materials include a non-metallic fibrous materials which may be coated with another non-metallic material such as wax and which may be layered between the foam interior 18 and latex exterior 20 or which may be integral to the foam interior 18. Additional embedded materials are beadlike objects made of materials such as wax, plastic, or sealed liquids or gels having image contrast which is dependent on the x-ray tube voltage (KVp).

As is described above, the preferred foam interior material 18 is preferably x-ray absorbant and preferably a spongy malleable foam. While most foams are generally x-ray transparent, it is preferred that the foam for the present invention include x-ray absorbant materials such as liquids, gels, and/or metal either (substantially) homogeneously distributed throughout the foam or layered on the surface of the foam. Such material can be provided, for example, via plastic paint containing x-ray absorbing metals. The only requirement is that the x-ray absorbing substance be located in the pathway of the x-rays when the simulator is imaged thereby causing the simulator to have the desired level of x-ray opacity.

As is shown in FIG. 1B, in one embodiment of the phantom 10 the breast simulators 14 are permanently fixed to the upper torso 12. As is shown in FIGS. 1A, 4A, and 4C, and described above, in a second embodiment of the phantom 10 the breast simulators 14 comprise a breast simulator unit 15 which is detachable from the upper torso 12 of the phantom 10. Having the breast simulators 14 as a detachable unit 15 enables mounting different breast simulators 14 to a single phantom 10 torso 12.

For example, breast simulator units 15 can be manufactured to include breast simulators 14 which mimic breast types varying in size, shape and internal construction. Breast simulators 14 can also be manufactured to simulate breast characteristics found in x-ray mammographic images, such as fibrils, lesions, dense regions, microcalcifications, and masses with calcification; as well as arteries and veins, adipose and glandular tissue etc. Breast simulators 14 can be constructed to simulate any desired tissue abnormality which can be imaged with x-ray mammography. Breast simulators 14 can also be constructed to simulate abnormalities of breast duct structures which are usually imaged through contrast enhanced mammography.

As is shown in FIGS. 4A and 4B, the torso 12 of the phantom 10 preferably includes a channel or indented area 40 into which the breast simulator unit 15 can be securely aligned. The breast simulator unit 15 can be securely tied around the torso 12 or, as is shown in FIGS. 4B, 4C, and 4D, the breast simulator unit 15 can be attached to the phantom 10 by an aperture and pin arrangement. Specifically, FIG. 4C shows that the breast simulator unit 15 preferably comprises a belt-like structure 42 to which the breast simulators 14 are attached. The belt structure 42 can have stretchable portions and, as is shown in FIG. 4C, preferably includes apertures 44. Furthermore, FIGS. 4B and 4D show that the back of the phantom 10 preferably includes pins 46 which correspond to the apertures 44 in the belt structure 42. To attach the breast simulator unit 15 to the torso 12 of the phantom 10 the belt 42 preferably is aligned with the channel 40 of the torso 12 and stretched around the torso 12 to hook the apertures 44 onto the pins 46. The combination of the channel 40 and the aperture/pin 44/46 arrangement allows the unit 15 to be tightly attached to the torso 12 such that the breast simulators 14 can be manipulated without substantially disturbing the positioning of the simulators 14 with respect to the torso 12.

The upper torso 12 of the phantom 10 also serves as a rib cage simulator (with simulated pectoralis major muscle) in addition to providing a mounting surface for the breast simulators 14 thereby providing an additional element of realistic patient simulation. The rib cage simulator and simulated pectoralis major muscle preferably comprise plastic material which is readily available and preferably are components of the torso portion 12 of the present phantom 10. In addition, as is shown in FIG. 4E, the breast simulator unit 15 includes a chest wall portion 48 which simulates a patient's chest wall and is useful in training technicians on the proper positioning of a patient as is described in greater detail below. As is also shown in FIG. 4E, the chest wall portion 48 is preferably at least slightly convex. In addition, it is preferred that the breast simulator unit 15 simulates any portion of the torso 10 which is "missing" due to inclusion of the indented area 40. For example, a portion of the simulated rib case (and pectoralis major muscle) of the torso 10 might be removed to incorporate the indented area 10 into the phantom 10 and, in such a case, the breast simulator unit 15 preferably includes that missing portion. Therefore, when the breast simulator unit 15 is mounted to the torso 10 (in the indented area 40) the full rib cage is simulated providing a realistic look and feel.

The anthropomorphic mammography phantom 10 of the present invention can be used for calibrating a mammography unit by imbedding in the breast simulators 14 structures 24, as shown in FIG. 4E, whose imaged contrast depends on the applied x-ray tube voltage (kVp). The maximum number of such structures or a distinct subset of these structures detected in a mammographic image can be used to indicate that the proper kVp and optimal x-ray exposure were used. Importantly, such structures help to test and train technologists in the proper placement and positioning of patients undergoing mammography.

One example of structures 24 whose imaged contrast depends on the applied kVp are bead-like objects made of materials such as wax, plastic, or sealed liquids, or sealed gels having image contrast which is kVp dependent. Detection of the images of these imbedded structures allows assessment of the applied kVp settings. In addition, these bead-like objects may be used to simulate cysts present in patient breast tissue.

Materials which include wool-like metal and non-metal fibrous materials (such as steel wool, aluminum wool, copper wool, cotton wool coated or soaked with special chemicals, plastic thread, coated plastic threads, etc.) can be distributed inside a breast simulator to produce mammographic images closely resembling patient x-ray mammography breast images depicting characteristic glandular and/or dense tissue. In addition, materials having a desired x-ray opacity x-ray opaque materials such as metal salt grains or grains of crushed egg shells preferably ranging in size from approximately 0.1 mm to approximately 2.0 mm in diameter can be imbedded inside a breast simulator 14 to produce mammographic images with features closely resembling patient breast images which include microcalcifications. The imbedded grains can be grouped into distinct patterns. In one embodiment, grains can be grouped in such a way so that their images overlap images of other grains and/or images of wool-like materials (described above) simulating dense tissue with microcalcifications. The grouping and/or overlap of such structures simulates the appearance of microcalcifications inside patient dense tissue.

In another embodiment, grains can be grouped to facilitate assessment of image resolution. The grain groupings need not be spaced or patterned in any particular or reproducible manner. The grains can be manufactured into the breast simulators 14 or they can be injected (e.g. using a needle and syringe) into a breast simulator 14 at a later time.

In yet another embodiment, fine metallic mesh strip(s) can be imbedded inside the breast simulator 14. The image of the mesh facilitates image resolution assessment. Mammography images of breast simulators which include thin, sub-millimeter metal wool, for instance, also aid in the assessment of system resolution. Contrast and resolution features found in existing devices and test phantoms that are required for compliance with the Mammography Quality Standards Act can be incorporated into the anthropomorphic mammography phantom of the present invention thereby enabling the anthropomorphic mammography phantom to also be utilized as a mammography calibration tool.

In yet another embodiment a breast simulator comprising a core material of spongy foam, the foam is impregnated with a liquid or gel having a desired x-ray opacity which improves x-ray radiographic characteristics for calibration purposes and further simulates the physical mass-like quality of actual breasts.

One implementation of the anthropomorphic mammography phantom 10 of the present invention simulates patient motion (such as breathing, heart beating, and blood flowing) by pulsing the phantom and thereby permitting x-ray technologists to assess the effect of patient motion on image quality. The phantom 10 can include tubing attachable to a simple pump which is used to pulse liquid or gas through the tubing to simulate patient motion. Yet another implementation of the anthropomorphic mammography phantom 10 simulates the effect of the heart pumping blood or blood with x-ray contrast dyes by embedding hollow tubes into the breast simulators 14 of the phantom 10. A pump is used to pulse and/or circulate the appropriate liquids. Realistic angiographic conditions are simulated by injecting an x-ray contrast dye into the circulating liquid.

The phantom 10 of the present invention can be mounted on a portable stand with adjustable height and inclination to aid in breast/phantom positioning. For example, as is shown in FIGS. 4A and 4B, the phantom 10 can be attached to a base 50 via a swivel support 52 which allows the phantom 10 to be tilted (preferably, e.g., 20–30 degrees) and allows the phantom 10 to be rotated.

Breast simulators 14 including imbedded material having image overlap can be used for training proper breast positioning and proper breast compression. As is shown in FIGS. 2A and 2B, proper breast compression resolves overlapping images. FIG. 2A shows a front view of a breast simulator 14 including underlying structures 26 being compressed using standard compression by two compression plates 28 and shows a resulting image 30. As is shown, the resulting image 30 includes overlap from the images of the underlying structures thereby producing a shadow which would typically be flagged as an abnormality by a radiologist interpreting the results. As is described below, proper compression would separate overlapping structures thereby providing improved diagnosis of the tissue (i.e. by resolving the images of the structures).

FIG. 2B shows a front view of the same breast simulator 14 and underlying structures 26 as in FIG. 2A and shows the resulting image 34. However, FIG. 2B shows the breast simulator 14 and structures 26 being compressed using spot compression between a lower compression plate 28 and a spot compressor 32. As is shown, the resulting spot-compression image 34 spreads out the x-ray images of the structures 26 thereby allowing proper interpretation of the image and subsequent diagnosis.

Figure 3A:
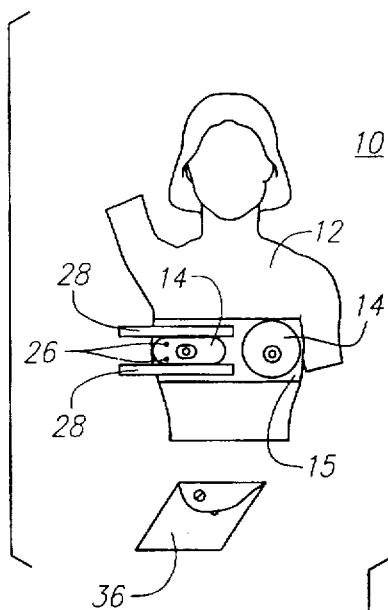
FIG. 3A is a front view of a breast phantom showing a breast simulator subjected to standard compression and an x-ray image showing unresolved overlap of tissue abnormalities in the breast simulator.
Figure 3B:
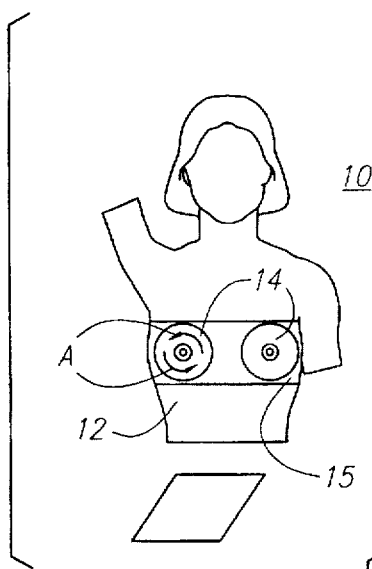
FIG. 3B is a front view of a breast phantom showing the breast simulator from FIG. 3A being rotated.
Figure 3C:
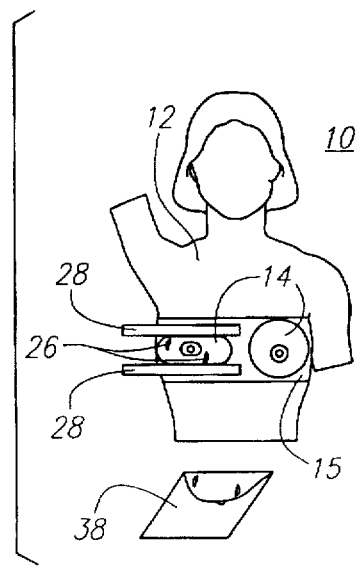
FIG. 3C is a front view of a breast phantom showing the rotated breast simulator from FIG. 3B subjected to standard compression and an x-ray image showing resolution and separation of the tissue abnormalities from FIG. 3A due to the rotation.

As is shown in FIGS. 3A and 3C, proper breast positioning also resolves overlapping images. FIG. 3A shows a front view of a breast simulator 14 including underlying structures 26 being held in a standard position by two compression plates 28 and shows a resulting image 36. As is shown, the resulting image 36 includes overlap from the images of the underlying structures 26 thereby producing a shadow which would typically be flagged as an abnormality by a radiologist interpreting the results. Proper breast re-positioning resolves the images thereby resolving the apparent abnormality. FIG. 3B shows repositioning the breast simulator 14 by rotating the top of the breast medially and the bottom of the breast laterally (as indicated by the arrows A in FIG. 3B).

FIG. 3C shows a front view of the breast simulator 14 and underlying structures 26 from FIG. 3A and shows the resulting image 38. However, FIG. 3C shows the breast simulator 14 and structures 26 after the breast simulator 14 was rotated as described above. As is shown, the resulting repositioned image 34 spreads out the images of the structures 26 thereby allowing proper interpretation of the image and subsequent analysis.

Both spot compression and breast rotation are techniques which are used to improve mammographic images. The anthropomorphic mammography phantom 10 of the present invention provides technicians an opportunity to realistically practice the compression and positioning techniques such as described above which currently available phantoms do not.

A further aspect of the present invention is to provide a lung phantom 64 as shown in FIG. 4H. Such a lung phantom 64 can be placed into a hollow cavity 60 in the torso 12 of typical available chest phantoms as shown in FIGS. 4F and 4G. As is described above, currently available chest phantoms generally attempt to duplicate a human torso, including bones, but do not furnish fine x-ray patterns as are generally produced in actual lung x-ray images because such phantoms merely typically include an empty, air-filled cavity 60 to simulate human lungs. The placement of a lung simulator 64 into the cavity of such a torso 12 enables the production of x-ray images similar to chest x-ray images of human patients including images showing fine structures, such as bronchial tubes, bronchiales, and lung tissue irregularities. This provides for developing and improving diagnostic skills of x-ray interpreters, for calibrating x-ray equipment, and for improving the x-ray imaging skills of x-ray technologists.

The lung simulator 64 is preferably made from the same materials described above for the breast simulator, however, a latex skin-like layer is unnecessary. For example, the lung simulator 64 preferably comprises a spongy foam material having the desired x-ray opacity, and which can include materials, such as wool-like metal, non-metal fibrose materials, metal salt grains (e.g. calcium or aluminum salt grains), and/or crushed egg shell grains, and carefully spread fine metal wool, imbedded in or glued on the foam, bead-like objects made of materials such as sealed liquids, sealed gels, wax or plastics. The lung simulator 64 is held in the torso cavity 60 of the chest phantom (shown in FIGS. 4F and 4G) by the force of the lung simulator 64 pressing against the walls forming the cavity 60 (i.e. the spongy simulator 64, which is larger than the cavity 60, is compressed and inserted in the cavity 60 and allowed to expand).

While embodiments of the present invention have been shown and described, various modifications may be made without departing from the scope of the present invention, and all such modifications and equivalents are intended to be covered.

What is claimed is:

1. An apparatus for mammography training and mammographic system calibration, said apparatus having anthropomorphic features and comprising
a substantially complete human-like upper torso, and
at least one breast simulator attached to the torso, said breast simulator comprising a material having human breast-like mechanical and x-ray radiographic imaging properties making the simulator suitable for at least one of mammography training and mammographic system calibration, wherein the breast simulator is at least one from the group of elastic foam, gel, and sponge.

2. The apparatus of claim 1 wherein the torso includes adjustable human-like upper arms.

3. The apparatus of claim 1 further comprising a stand to which the torso is mounted, said stand enabling adjustable positioning of the torso.

4. The apparatus of claim 1 wherein the at least one breast simulator is detachable from the torso.

5. The apparatus of claim 4 comprising at least two detachable breast simulators wherein the breast simulators comprise one or more shape, size, mammographic x-ray opacity, composition, stiffness, pendulousity, hardness, elasticity, compressibility, resiliency, and restitution.

6. The apparatus of claim 1 comprising at least two breast simulators wherein the simulators comprise one or more shape, size, mammographic x-ray opacity, composition, stiffness, pendulousity, hardness, elasticity, compressibility, resiliency, and restitution, and simulate one or more regular breast tissue, irregular breast tissue, a breast implant, and a breast with contrast enhancing dye under x-ray exposure.

7. The apparatus of claim 1 wherein the breast simulator material further comprises wool-like material.

8. The apparatus of claim 7 wherein the wool-like material is at least one from the group consisting of steel wool, aluminum wool, copper wool, treated cotton wool, and plastic wool.

9. The apparatus of claim 1 further comprising at least one object having a desired x-ray opacity imbedded in the breast simulator and comprising one or more size, shape, mammographic x-ray opacity, and radiological x-ray contrast.

10. The apparatus of claim 9 wherein the at least one object imbedded in the breast simulator comprises at least one bead-like object.

11. The apparatus of claim 9 wherein the at least one object imbedded in the breast simulator comprises one or more grains.

12. The apparatus of claim 11 wherein the one or more grains are one or more from the group consisting of a sodium chloride grain, a calcium salt grain, an aluminum salt grain, and a crushed egg shell grain.

13. The apparatus of claim 11 comprising more than one grains imbedded in the breast simulator in a distinct pattern.

14. The apparatus of claim 9 wherein the at least one object imbedded in the breast simulator comprises a piece of fine metallic mesh.

15. The apparatus of claim 1 further comprising tubing embedded in the breast simulator and attached to a pump for circulating at least one of liquids and gasses through the tubing.

16. An apparatus for training and image quality evaluation comprising at least one lung simulator simulating x-ray properties of a human lung and comprising at least one material having x-ray radiographic imaging properties of at least one of regular human lung tissue and irregular human lung tissue wherein said properties make the simulator suitable for at least one of training on and image quality evaluation of general diagnostic radiology equipment, wherein the lung simulator is at least one from the group of eleastic foam, gel, and sponge.

17. The apparatus of claim 16 wherein the lung simulator material further comprises wool-like material.

18. The apparatus of claim 17 wherein the wool-like material is at least one from the group consisting of steel wool, aluminum wool, copper wool, treated cotton wool, and plastic wool.

19. The apparatus of claim 16 further comprising at least one object imbedded in the lung simulator.

20. The apparatus of claim 19 wherein the at least one object imbedded in the lung simulator comprises at least one wool-like material.

21. The apparatus of claim 19 wherein the at least one object imbedded in the lung simulator comprises at least one bead-like object comprising one or more size, shape, radiographic x-ray opacity, and radiological x-ray contrast.

22. The apparatus of claim 19 wherein the at least one object imbedded in the lung simulator comprises one or more grains.

23. The apparatus of claim 22 wherein the one or more grains are one or more from the group consisting of a sodium chloride grain, a calcium salt grain, an aluminum salt grain, and a crushed egg shell grain.

24. The apparatus of claim 22 comprising more than one grains imbedded in the lung simulator in a distinct pattern.

25. The apparatus of claim 19 wherein the at least one object imbedded in the lung simulator comprises a piece of fine metallic mesh.

26. The apparatus of claim 16 wherein the lung simulator comprises foam and further comprising at least one x-ray opaque object imbedded in the foam.

27. The apparatus of claim 26 wherein the at least one object is at least one from the group consisting of wool-like material, steel wool, aluminum wool, copper wool, treated cotton wool, plastic wool, a bead-like object, one or more grains, a sodium chloride grain, a calcium salt grain, an aluminum salt grain, and a crushed egg shell grain.

28. An apparatus for mammography training and mammographic system calibration, said apparatus having anthropomorphic features and comprising
a substantially complete human-like upper torso, and
at least one breast simulator attached to the torso, said breast simulator comprising a material having human breast-like mechanical and x-ray imaging radiographic properties making the simulators suitable for at least one of mammography training and mammographic system calibration, wherein the simulators comprise one or more shape, size, mammographic x-ray opacity, composition, stiffness, pendulousity, hardness, elasticity, compressibility, resiliency, and restitution, and simulate one or more regular breast tissue, irregular breast tissue, a breast implant, and a breast with contrast enhancing dye under x-ray exposure.

29. An apparatus for mammography training and mammographic system calibration, said apparatus having anthropomorphic features and comprising a substantially complete human-like upper torso, and at least two detachable breast simulators attached to the torso, said breast simulators comprising a material having human breast-like mechanical and x-ray radiographic imaging properties making the simulators suitable for at least one of mammography training and mammographic system calibration, and wherein the breast simulators comprise one or more shape, size, mammographic x-ray opacity, composition, stiffness, pendulousity, hardness, elasticity, compressibility, resiliency, and restitution.

30. An apparatus for mammography training and mammographic system calibration, said apparatus having anthropomorphic features and comprising a substantially complete human-like upper torso, and at least two breast simulators attached to the torso, said breast simulators comprising a material having human breast-like mechanical and x-ray imaging radiographic properties making the simulators suitable for at least one of mammography training and mammographic system calibration, wherein the simulators comprise one or more shape, size, mammographic x-ray opacity, composition, stiffness, pendulousity, hardness, elasticity, compressibility, resiliency, and restitution, and simulate one or more regular breast tissue, irregular breast tissue, a breast implant, and a breast with contrast enhancing dye under x-ray exposure.

31. An apparatus for mammography training and mammographic system calibration, said apparatus having anthropomorphic features and comprising a substantially complete human-like upper torso, and at least one breast simulator attached to the torso, said breast simulator comprising a material having human breast-like mechanical and x-ray imaging radiographic properties making the simulator suitable for at least one of mammography training and mammographic system calibration, wherein the breast simulator material comprises a wool-like material and elastic foam, and wherein the wool-like material comprises at least one of steel wool, aluminum wool, copper wool, treated cotton wool, and plastic wool.

32. An apparatus for mammography training and mammographic system calibration, said apparatus having anthropomorphic features and comprising a substantially complete human-like upper torso, at least one breast simulator attached to the torso, said breast simulator comprising a material having human breast-like mechanical and x-ray imaging radiographic properties making the simulator suitable for at least one of mammography training and mammographic system calibration, and at least one object having a desired x-ray opacity imbedded in the breast simulator and comprising one or more size, shape, mammographic x-ray opacity, and radiological x-ray contrast, and wherein the at least one object imbedded in the breast simulator comprises a piece of fine metallic mesh.

33. An apparatus for mammography training and mammographic system calibration, said apparatus having anthropomorphic features and comprising a substantially complete human-like upper torso, at least one breast simulator attached to the torso, said breast simulator comprising a material having human breast-like mechanical and x-ray imaging radiographic properties making the simulator suitable for at least one of mammography training and mammographic system calibration, and tubing embedded in the breast simulator and attached to a pump for circulating at least one of liquids and gasses through the tubing.

34. An apparatus for training and system calibration comprising at least one lung simulator simulating x-ray radiographic imaging properties of a human lung and comprising at least one material having x-ray radiographic imaging properties similar to at least one of regular human lung tissue and irregular human lung tissue wherein said properties make the simulator suitable for at least one of training on and image quality evaluation of of diagnostic radiology equipment, wherein the lung simulator material comprises a wool-like material and foam, and wherein wool-like material comprises at least one of steel wool, aluminum wool, copper wool, treated cotton wool, and plastic wool.

35. An apparatus for training and system calibration comprising at least one lung simulator simulating x-ray radiographic imaging properties of a human lung and comprising at least one material having x-ray radiographic imaging properties similar to at least one of regular human lung tissue and irregular human lung tissue wherein said properties make the simulator suitable for at least one of training on and image quality evaluation of diagnostic radiology equipment, and at least one object having a desired x-ray opacity imbedded in the lung simulator, wherein the at least one object imbedded in the lung simulator comprises at least one wool-like material.

36. An apparatus for training and system calibration comprising at least one lung simulator simulating x-ray radiographic imaging properties of a human lung and comprising at least one material having x-ray radiographic imaging properties similar to at least one of regular human lung tissue and irregular human lung tissue wherein said properties make the simulator suitable for at least one of training on and image quality evaluation of diagnostic radiology equipment, and at least one object having a desired x-ray opacity imbedded in the lung simulator, wherein the at least one object imbedded in the lung simulator comprises a piece of fine metallic mesh.

37. An apparatus for mammography training and mammographic system calibration, said apparatus having anthropomorphic features and comprising a substantially complete human-like upper torso, and at least one detachable breast simulator attached to the torso, said breast simulator comprising a material having human breast-like mechanical and x-ray imaging radiographic properties making the simulators suitable for at least one of mammography training and mammographic system calibration, and wherein the breast simulators comprise one or more shape, size, mammographic x-ray opacity, composition, stiffness, pendulousity, hardness, elasticity, compressibility, resiliency, and restitution.

* * * * *

UNITED STATES PATENT AND TRADEMARK OFFICE
CERTIFICATE OF CORRECTION

PATENT NO. : 5,719,916
DATED : February 17, 1998
INVENTOR(S) : Nelson et al.

It is certified that error appears in the above-identified patent and that said Letters Patent is hereby corrected as shown below:

In the Claims

In column 12, line 22, delete "of of" and insert therefor -of-.

In column 12, line 24, after "wherein" insert -the-.

In column 10, line 25, delete "eleastic" and insert -elastic-

In column 11, lines 1, 31, 47 and 60 and column 12, lines 9 and 59-60, delete "imaging radiographic" and insert therefor -radiographic imaging-.

Signed and Sealed this

Eleventh Day of August 1998

Attest:

BRUCE LEHMAN

*Attesting Officer*  *Commissioner of Patents and Trademarks*